(12) United States Patent
Kim et al.

(10) Patent No.: US 10,023,664 B2
(45) Date of Patent: Jul. 17, 2018

(54) POLYMER

(71) Applicant: LG Chem, Ltd., Seoul (KR)

(72) Inventors: Su Jeong Kim, Daejeon (KR); Jeong Ae Yoon, Daejeon (KR); Sung Soo Yoon, Daejeon (KR); Kyong Seob Kim, Daejeon (KR); Khee Hwan Choi, Daejeon (KR); Hae Seok Chae, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/503,915

(22) PCT Filed: Dec. 15, 2015

(86) PCT No.: PCT/KR2015/013738
§ 371 (c)(1),
(2) Date: Feb. 14, 2017

(87) PCT Pub. No.: WO2016/099120
PCT Pub. Date: Jun. 23, 2016

(65) Prior Publication Data
US 2017/0275398 A1    Sep. 28, 2017

(30) Foreign Application Priority Data

Dec. 15, 2014 (KR) .................. 10-2014-0180726

(51) Int. Cl.
*C08F 220/18* (2006.01)
*C08F 220/28* (2006.01)
*C08F 20/18* (2006.01)

(52) U.S. Cl.
CPC ................. *C08F 20/18* (2013.01)

(58) Field of Classification Search
CPC .............. C08F 220/18; C08F 2220/1883
See application file for complete search history.

(56) References Cited

U.S. PATENT DOCUMENTS

| | | | |
|---|---|---|---|
| 3,565,814 A * | 2/1971 | Pellon | G03C 1/685 252/586 |
| 5,061,481 A | 10/1991 | Suzuki et al. | |
| 5,708,110 A | 1/1998 | Bennett et al. | |
| 6,024,950 A | 2/2000 | Takada et al. | |
| 2009/0196839 A1 * | 8/2009 | Farcet | A61K 8/04 424/59 |

FOREIGN PATENT DOCUMENTS

| | | |
|---|---|---|
| CN | 103189404 A | 7/2013 |
| JP | H11116459 A | 4/1999 |
| JP | 2000119140 | 4/2000 |
| JP | 2001181123 | 7/2001 |
| JP | 2003055136 | 2/2003 |
| JP | 2003171431 A | 6/2003 |
| JP | 2004075755 A | 3/2004 |
| JP | 2009191068 A | 8/2009 |
| WO | 2007123789 A2 | 11/2007 |

OTHER PUBLICATIONS

Machine translation of JP 2003-171431.*
Aldrich Reference of Polymer Properties.*
Dielectric Constants, downloaded from https://depts.washington.edu/eooptic/linkfiles/dielectric_chart%5B1%5D.pdf.*
Solubility of Homopolymers in Common Solvents, downloaded from polymersource.com on Mar. 2, 2018.*
Rivaldi et al., Journal of Polymer Science, Part A; Polymer Chemistry 2009, 47, 3045-3055.*
International Search Report from PCT/KR2015/013738, dated Apr. 11, 2016.
Extended European Search Report for Application No. EP15870287 dated Jan. 3, 2018.
Chinese Search Report for Application No. CN201580045731.0 dated Apr. 20, 2018.

* cited by examiner

*Primary Examiner* — Vu A Nguyen
(74) *Attorney, Agent, or Firm* — Lerner, David, Littenberg, Krumholz & Mentlik, LLP

(57) ABSTRACT

The present application relates to a polymer and a use thereof. The present application may provide a functional polymer which expresses a low solubility to a polar solvent and a non-polar solvent. If applied to the use of cosmetics such as mascara or to medical uses, the polymer in the present application may express a tolerance to diverse solvents such as sebum, sweat, tears and the like, and thus enables makeup to last, etc. Accordingly, the polymer may be applied to diverse uses and used in film forming agents, cosmetic compositions, or cosmetics, or the like.

15 Claims, No Drawings

POLYMER

CROSS-REFERENCE TO RELATED APPLICATIONS

The present application is a national phase entry under 35 U.S.C. § 371 of International Application No. PCT/KR2015/013738, filed Dec. 15, 2015, which claims of priority from Korean Patent Application No. 2014-0180726 filed on Dec. 15, 2014, the disclosures of which are herein incorporated by reference.

TECHNICAL FIELD

The present application relates to a polymer and a film forming agent comprising the polymer.

Background Art

There is a case that functional polymers are required in preparing cosmetics or drugs. For example, in cosmetics such as mascara, or cosmetics or drugs that are applied to other skins, polymers having resistance to solvents of different properties such as sweat, tears and sebum may be required. Polymers, which are applied in preparing cosmetics, are described in Patent Documents 1 and 2.

PRIOR ART DOCUMENTS

Patent Documents

Patent Document 1: Japanese Unexamined Patent Publication No. 2000-119140
Patent Document 2: Japanese Unexamined Patent Publication No. 2003-055136

DISCLOSURE

Technical Problem

The present application provides a polymer and a film forming agent comprising the polymer. It is one main object of the present application to provide a functional polymer which is applied to cosmetics, such as mascara, or articles to be used in human bodies, such as medical supplies, by exhibiting a low solubility in both polar solvents and non-polar solvents to have resistance to sweat and sebum and the like and a film forming ability suitable to the above applications, and a use thereof.

Technical Solution

The polymer of the present application exhibits a low solubility in polar solvents and non-polar solvents. In the present application, the term non-polar solvent means a solvent having a dielectric constant at 25° C. in a range of about 1 to about 3, about 1.5 to 2.5 or about 1.5 to 2 or so, and the term polar solvent means a solvent having a dielectric constant at 25° C. in a range of about 75 to about 85 or about 75 to 80. A representative example of the non-polar solvent is hexane (dielectric constant (25° C.): about 1.89), and a representative example of the polar solvent is water (dielectric constant (25° C.): about 78.54), without being limited thereto. In chemistry, the dielectric constant for the solvent is known for each solvent.

In one example the polymer may have solubility in the polar solvent of 10 or less, or 5 or less. In one example the polymer may have solubility in the non-polar solvent of 10 or less, or 5 or less. It means that the lower the value of the solubility, the polymer has more excellent resistance against the corresponding solvent, so that the lower limit is not particularly limited. For example, the solubility in the polar solvent and the non-polar solvent may be about 0.001 or more, about 0.01 or more, about 0.1 or more, or about 1 or more, respectively. In the present application, solubility in a specific solvent refers to grams (g) of a polymer that can be dissolved in 100 g of the corresponding solvent as much as possible. Furthermore, unless otherwise specified, the solubility in the present application refers to solubility measured at room temperature. In the present application the term room temperature is a natural temperature without warming or cooling, and for example, may be a temperature in a range of about 10° C. to 30° C., about 15° C. to 30° C., or about 20° C. to 30° C., or a temperature of about 25° C. or so. In the case of the characteristic, the value of which varies depending on temperatures, such as the solubility, among characteristics mentioned in this specification, the corresponding characteristic is a characteristic at room temperature, unless otherwise specified.

The polymer can exhibit solubility in the intermediate step solvents between the polar and non-polar solvents. For example, the polymer may have solubility in a range of 15 or more or about 15 to 50 in the solvent having a dielectric constant at 25° C. in a range of 4 to 15, 5 to 15, 5 to 10, 5 to 8 or about 5 to 6.5. Such a solvent may be exemplified by ethyl acetate (dielectric constant (25° C.): about 6.02) and the like, without being limited thereto.

The polymer may be, for example, through adjusting the types of monomers forming the polymer and the proportions thereof.

For example, the polymer may comprise polymerized units of a first monomer having a homopolymer solubility parameter of less than 10.0 $(cal/cm^3)^{1/2}$ and polymerized units of a second monomer of less than 10.0 $(cal/cm^3)^{1/2}$ or more.

In the present application the solubility parameter refers to a solubility parameter of a homopolymer prepared by polymerizing the corresponding monomer, through which the degree of hydrophilicity and hydrophobicity in the corresponding monomer may be found out. A method of obtaining the solubility parameter is not particularly limited, and may be in accordance with a method known in the art. For example, the parameter may be calculated or obtained according to the method known in the art as the so-called HSP (Hansen solubility parameter). Here, in another example, the homopolymer solubility parameter of the first monomer may be in a range of 5 $(cal/cm^3)^{1/2}$ to 9.5 $(cal/cm^3)^{1/2}$ or 7 $(cal/cm^3)^{1/2}$ to 9 $(cal/cm^3)^{1/2}$. Here, in another example, the homopolymer solubility parameter of the second monomer may be in a range of 10 $(cal/cm^3)^{1/2}$ to 15 $(cal/cm^3)^{1/2}$ or 10 $(cal/cm^3)^{1/2}$ to 13 $(cal/cm^3)^{1/2}$. By appropriately applying the monomers having solubility parameters of these ranges, it is possible to form the polymer representing the above-described characteristics.

In addition, in the present application the polymerized unit of any monomer or compound means a form in which the monomer or compound is included in the polymer as a monomer unit via a polymerization reaction.

The monomer usable as the first monomer by having the above solubility parameter may be exemplified by alkyl (meth)acrylate or aromatic (meth)acrylate. In the present application the term (meth)acrylate may mean acrylate or methacrylate.

An alkyl group included in the alkyl (meth)acrylate may be exemplified by a straight, branched or cyclic alkyl group having 1 to 20 carbon atoms, 4 to 20 carbon atoms, 8 to 20 carbon atoms or 10 to 20 carbon atoms and the alkyl group may be optionally substituted by one more substituents. Such a monomer may be exemplified by methyl (meth)acrylate, ethyl (meth)acrylate, n-propyl (meth)acrylate, isopropyl (meth)acrylate, n-butyl (meth)acrylate, t-butyl (meth)acrylate, sec-butyl (meth)acrylate, pentyl (meth)acrylate, 2-ethylhexyl (meth)acrylate, 2-ethylbutyl (meth)acrylate, n-octyl (meth)acrylate, isobutyl isobornyl (meth)acrylate, isooctyl (meth)acrylate, isononyl (meth)acrylate or lauryl (meth)acrylate, or the like, without being limited thereto.

The aromatic (meth)acrylate may be exemplified by aryl (meth)acrylate or arylalkyl (meth)acrylate. Here, an aryl group of aryl or arylalkyl may be, for example, an aryl group having 6 to 24 carbon atoms, 6 to 18 carbon atoms or 6 to 12 carbon atoms. In addition, an alkyl group of the arylalkyl may be, for example, an alkyl group having 1 to 20 carbon atoms, 1 to 16 carbon atoms, 1 to 12 carbon atoms, 1 to 8 carbon atoms or 1 to 4 carbon atoms. Here, the alkyl group may be straight, branched or cyclic, and the alkyl group or the aryl group may be optionally substituted by one or more substituents.

The aryl group or arylalkyl group can be exemplified by a phenyl group, a phenylethyl group, a phenylpropyl group or a naphthyl group, but is not limited thereto.

The first monomer may be exemplified, for example, by a compound represented by Formula 1 below.

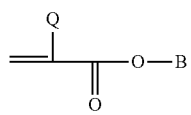

[Formula 1]

In Formula 1 Q may be hydrogen or an alkyl group, and B may be a straight or branched alkyl group having 4 or more carbon atoms or a alicyclic hydrocarbon group, or an aromatic substituent such as the aryl group or the arylalkyl group.

In Formula 1, the alkyl group present in Q may be exemplified by an alkyl group having 1 to 20 carbon atoms, 1 to 16 carbon atoms, 1 to 12 carbon atoms, 1 to 8 carbon atoms or 1 to 4 carbon atoms. The alkyl group may be straight, branched or cyclic. The alkyl group may be optionally substituted with one or more substituents.

In Formula 1, B may be a straight or branched alkyl group having 4 or more carbon atoms, 6 or more carbon atoms or 8 or more carbon atoms. Such a compound comprising the relatively long-chain alkyl group is known as a hydrophobic compound. The upper limit of the number of carbon atoms in the straight or branched alkyl group is not particularly limited, and for example, the alkyl group may be an alkyl group having up to 20 carbon atoms.

In another example, B in Formula 1 may be an alicyclic hydrocarbon group, for example, an alicyclic hydrocarbon group having 3 to 20 carbon atoms, 3 to 16 carbon atoms or 6 to 12 carbon atoms, and an example of such a hydrocarbon group may be exemplified by an alicyclic alkyl group, and the like, having 3 to 20 carbon atoms, 3 to 16 carbon atoms or 6 to 12 carbon atoms such as a cyclohexyl group or an isobornyl group. Such a compound comprising the alicyclic hydrocarbon group is also known as a relatively hydrophobic compound.

In the present application, the substituent, which may be optionally substituted on an alkyl group, an alkylene group, an aromatic substituent in Formula 1 above, or Formula 2 or 3 to be described below, may be exemplified by halogen such as chlorine or fluorine, a glycidyl group, an epoxy group such as an epoxyalkyl group, a glycidoxypropyl group or an alicyclic epoxy group, an acryloyl group, a methacryloyl group, an isocyanate group, a thiol group, an alkyl group, an alkenyl group, an alkynyl group or an aryl group, and the like, but is not limited thereto.

An appropriate type may be selected from the above monomers in consideration of the physical properties of the desired polymer and used.

As the second monomer, it is possible to use a monomer selected from monomers known to have the above described solubility parameter.

For example, as the second monomer, a compound represented by Formula 2 or 3 below may be used.

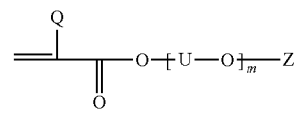

[Formula 2]

In Formula 2, Q is hydrogen or an alkyl group, U is an alkylene group, Z is hydrogen or an alkyl group, and m is any number:

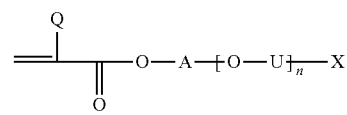

[Formula 3]

In Formula 3, Q is hydrogen or an alkyl group, A and U are each independently an alkylene group, X is a hydroxy group or a cyano group and n is any number.

In Formulas 2 and 3, the alkylene group may be exemplified by an alkylene group having 1 to 20 carbon atoms, 1 to 16 carbon atoms, 1 to 12 carbon atoms, 1 to 8 carbon atoms or 1 to 4 carbon atoms. The alkylene group may be straight, branched or cyclic. The alkylene group may be optionally substituted by one or more substituents.

In Formulas 2 and 3, the alkyl group present in Q and Z may be exemplified by an alkyl group having 1 to 20 carbon atoms, 1 to 16 carbon atoms, 1 to 12 carbon atoms, 1 to 8 carbon atoms or 1 to 4 carbon atoms. The alkyl group may be straight, branched or cyclic. In addition, the alkyl group may be optionally substituted with one or more substituents.

In Formulas 2 and 3, m and n may be any number, and for example, each independently a number in a range of 1 to 100, 1 to 90, 1 to 80, 1 to 70, 1 to 60, 1 to 50, 1 to 40, 1 to 30, 1 to 20, 1 to 16 or 1 to 12.

In one example, as the second monomer, a compound, wherein in Formula 2 above Q is hydrogen or an alkyl group having 1 to 4 carbon atoms, U is an alkylene group having 1 to 4 carbon atoms, Z is hydrogen or an alkyl group having 1 to 4 carbon atoms, and m is 1 to 30, may be used, but is not limited thereto.

The polymer may be prepared by polymerizing the first and second monomers in an appropriate ratio. For example, the polymer may comprise 50 to 99.9 parts by weight of the polymerized units of the first monomer and 0.1 to 20 parts by weight of the polymerized units of the second monomer. Here, in another example, the polymerized units of the first monomer may exist in 60 to 99.9 parts by weight, 70 to 99.9 parts by weight or 80 to 99.9 parts by weight. In addition, the polymerized units of the second monomer may be contained in 5 to 20 parts by weight or 7 to 20 parts by weight. In the present application, the unit part by weight may mean a ratio of weight between the respective components, unless otherwise specified. Furthermore, the weight ratio of the polymerized units of the monomer may mean the weight ratio of the monomer applied on preparing the polymer. Thus, for example, the phrase the polymer comprises 50 to 99.9 parts by weight of polymerized units of the first monomer and 0.1 to 20 parts by weight of polymerized units of the second polymer may mean that the polymer has been formed by polymerizing the monomer mixture comprising the first monomer and the second monomer in a weight ratio of 50~99.9:0.1~20 (first monomer: second monomer). If the weight ratio of the second monomer in the polymer is less than 0.1 parts by weight or the weight ratio of the first monomer is more than 99.9 parts by weight, the resistance to the oil-based solvent or the sebum proofness may not be enough, and if the weight ratio of the second monomer exceeds 20 parts by weight or the weight ratio of the first monomer is less than 50 parts by weight, the polymer cannot be formed by the phase separation, or the resistance to the polar solvent or the resistance to sweat or tears may not be enough.

In another example, the polymer may comprise at least 50%, at least 55%, at least 60%, at least 65%, at least 70%, at least 75% or at least 80%, of polymerized units of the first monomer, based on weight. The ratio of polymerized units of the first monomer may be 99% or less, 98% or less, 97% or less, 96% or less, 95% or less, 94% or less, 93% or less, 92% or less, 91% or less, or 90% or less, based on weight. In the above state, the polymer may comprise the polymerized units of the second monomer in a ratio of 40 parts by weight or less, 35 parts by weight or less, 30 parts by weight or less, 25 parts by weight or less, 20 parts by weight or less, 15 parts by weight or less, 10 parts by weight or less or about 8 parts by weight or less relative to 100 parts by weight of the polymerized units of the first monomer. The polymerized units of the second monomer may be contained in a ratio of at least about 0.1 parts by weight, at least 0.15 parts by weight, at least 0.2 parts by weight or at least 5 parts by weight ratio relative to 100 parts by weight of the polymerized units of the first monomer. While the resistance to the oil-based solvent or the sebum proofness is secured in the above ratio, the resistance to the polar solvent, or the resistance to sweat or tears or the like can be also effectively secured.

The polymer may comprise additional monomers for imparting other functions, for example, controlling glass transition temperature, etc. in addition to the above-described first and second monomers.

The polymer can be produced by a known polymerization method using the first and second monomers. In one example the polymer may be prepared by a solution polymerization method using a solvent, for example, an organic solvent, for example a radical solution polymerization method. For example, when the polymer is applied to an application in contact with a human body such as cosmetics, as a solvent in the polymerization process, a solvent friendly to the human body can be selected and used. Such a solvent may be exemplified by isododecane, isoparaffin or isohexadecane, and the like, but is not limited thereto.

In the present application the polymer may have a weight average molecular weight (Mw) in a range of 10,000 to 500,000. In the present application, the weight average molecular weight may be, for example, a converted value of the standard polystyrene measured using GPC (Gel Permeation Chromatograph), and the term molecular weight can refer to the weight average molecular weight, unless otherwise specified. For example, when the polymer is applied as a film forming agent, the above molecular weight (Mw) may be useful. By using the polymer in the above molecular weight (Mw) range, it is possible to form a film efficiently without an agglomeration phenomenon and the like.

In the present application the polymer may have a glass transition temperature of 10° C. or more. In another example, the glass transition temperature may be 15° C. or more, 20° C. or more, 25° C. or more, or 30° C. or more. The glass transition temperature of the polymer may be about 110° C. or less, about 100° C. or less, 90° C. or less, 80° C. or less, 70° C., 60° C. or less, or 55° C. or less. In the present application, the glass transition temperature is a theoretical value obtained through the so-called Fox equation from the monomer composition of the polymer. For example, when the polymer is applied as a film forming agent, the above glass transition temperature may be useful. By using the polymer in the above glass transition temperature range, it is possible to form a film efficiently without a stickiness or brittleness phenomenon and the like.

The present application also relates to a film forming agent, a cosmetic composition or a cosmetic, comprising the polymer. If the above-described polymer is used, it is possible to form a uniform film (coating) by application, to exhibit high stability even when applied to skin, and to show excellent resistance to various solvents such as sweat, tears or sebum by exhibiting a resistance to both polar and non-polar solvents.

Accordingly, the polymer can be applied to prepare a film forming agent or a cosmetic composition capable of being used in producing various cosmetics, including, cosmetic packs, make-ups, such as mascara, applied to lips or eyes, nail polishes which can be applied to fingernails or toenails, lipsticks, eye shadows, hair styling products or eyeliners, etc. In addition, the polymer or the film forming agent or the like may also be applied to a medicinal use, and the medicinal use may be exemplified by bandages or transdermal absorption formulations and the like.

The ratio of the polymer in the film forming agent, the cosmetic composition or the cosmetic is not particularly limited, which may be selected in consideration of application purpose. For example, if the polymer is applied to the cosmetic composition, the concentration of the polymer in the composition may be in the range of 1% by weight to 20% by weight, but is not limited thereto.

The film forming agent, the cosmetic composition or the cosmetic may further comprise other active ingredients depending on applications. Additional active ingredients may also be exemplified by medicinal ingredients, physiologically active ingredients or pharmacologically active ingredients as well as cosmetic ingredients such as whitening or sunscreen. Such an active ingredient may be exemplified by topical anesthetic ingredients (lidocaine, dibucaine hydrochloride, dibucaine, ethyl aminobenzoate, etc.), analgesic ingredients (salicylic acid derivatives such as methyl salicylate, indomethacin, piroxicam, ketoprofen, felbinac, etc.), anti-inflammatory ingredients (glycyrrhizinic acid, salts glycyrrhizinate such as dipotassium glycyrrhizinate, glycyrrhetinic acid, stearyl glycyrrhetinate, bufexamac, benzyl nicotinate, hydrocortisone, hydrocortisone butyrate, hydrocortisone acetate, prednisone valeroacetate, prednisone acetate, prednisone, dexamethasone, dexamethasone acetate, dimethyl isopropyl azulene ibuprofenpiconol, amika extract, *Scutellaria Baicalensis* Root extract, cattail ear extract, chamomile extract, calamine, licorice extract, guaiazulene, *gardenia* extract, *gentiana* extract, black tea extract, tocopherol, tocopheryl acetate, *lithospermum* extract, *perilla* extract, peony extract, sage extract, *Swertia japonica* extract, Mulberry Root extract, pyridoxine hydrochloride, peach leaf extract, cornflower extract, *saxifrage* extract, mugwort extract, roman chamomile extract, etc.), anti-histamine ingredients (chlorpheniramine maleate, diphenhydramine, diphenhydramine hydrochloride, diphenhydramine salicylate, ISO pen zyl hydrochloride, etc.), local irritation ingredients (ammonia, 1-menthol, dl-can full, peppermint oil, nicotinic acid, benzyl niconinate, nonylic acid vanilylamide, etc.), antipruritic ingredients (crotamiton etc.), preservative or sterilizing ingredients (acrinol, chlorhexidine gluconate, chlorhexidine hydrochloride, benzalkonium chloride, benzethonium chloride, povidone iodine, iodoform, iodine, potassium iodide, merbromin, oxides, cresol, triclosan, phenol, isopropyl methyl phenol, thymol, sodium salicylate, undecylenic acid, photosensitizer, hinokitiol, phenoxyethanol, chlorobutanol, quaternium 73, zinc pyrithione, para-hydroxybenzoic acid esters, eucalyptus extract, resorcin rosemary extract, etc.), antifungal ingredients (imidazole-based antifungal agenst, such as clotrimazole, clotrimazole acetate, miconazole acetate, econazole acetate, befornazole, oxiconazole acetate, sulconazole acetate, neticonazole hydrochloride, befornazole and tioconazole, omoconazole acetate, allylamine-based antifungal agents, such as terbinafine, terbinafine hydrochloride and naftifine, benzylamine-based antifungal agents such as butenafine, allylamine-based antifungal agents such as amorphin hydrochloride, thiocarbamic acid-based antifungal agents such as tolnaftate, tolciclate, pyrrolnitrine, exalamide, cyclopirox olamine, etc.), tissue-repairing ingredients (allantoin, heparin-like substances, vitamin A palmitate, vitamin D2, retinol acetate, retinol, vitamin A oil, panthenol, etc.), astringent ingredients (zinc oxide, *Acanthopanax senticosus* extract, aluminum chloride, yellow gourd extract, salts thereof, citric acid, white birch extract, tea extract, hop extract, horse chestnut extract, etc.), dead skin flexibilizer ingredients (urea, glycerin, concentrated glycerin, potassium hydroxide, salicylic acid, sulfur, colloidal sulfur, resorcin, glycolic acid, lactic acid, sodium sulfate, etc.), moisturizing ingredients (butylene glycol, pyrrolidone sodium carboxylate, propylene glycol, ribonucleic acid sodium, *Angelica utilis* extract, asparaginic acid, alanine, arginine, sodium alginate, *althaea* extract, *aloe vera* extract, oyster-extract, hydrolyzed keratin, hydrolyzed collagen, hydrolyzed conchiolin, hydrolyzed egg shell membrane, hydrolyzed albumen, hydrolyzed silk, brown algae extract, quince extract, bramble extract, xylitol, chitosan, cucumber extract, quince seed extract, glycine, glycerin, glucose, cape aloe extract, cystin, cysteine, mallow extract, serine, sorbitol, trehalose, sodium lactate, sodium hyaluronate, placenta extract, sponge gourd extract, multi fee, mannitol, lily extract, lactoferrin, lysine, apple extract, royal jelly extract, etc.), emollient ingredients (almond oil, avocado oil, olive oil, oleic acid, orange roughy oil, cacao butter, carrot extract, squalane, ceramide, evening primrose oil, grape seed oil, jojoba oil, macadamia nut oil, mineral oil, mink oil, eucalyptus oil, rosehip oil, vaseline, etc.), whitening ingredients (ascorbic acid, ascorbic acid derivatives, arbutin, recinol, ellagic acid, glutathione, kojic acid, rose fruit extract, kiwi extract, etc.), ultraviolet protective ingredients (para-aminobenzoic acid, para-aminobenzoic acid ethyl ester, para-aminobenzoic acid glycerin ester, para-dimethylaminobenzoic acid amyl alcohol ester, para-dimethylaminobenzoic acid 2-ethylhexyl alcohol ester, t-butylmethoxydibenzoyl methane, oxybenzones, octyl triazone, octyl salicylate, ethyl diisopropyl cinnamate, methyl diisopropyl cinnamate, cinoxate, dimethoxy cinnamic acid glyceryl octanate, octyl dimethoxy benzylidene dioxoimidazolidine propionate, Chinese tea extract, drometrizole, isopropyl para-methoxycinnamate, homosalate, octyl methoxy cinnamate, etc.), herbal extract ingredients, vitamins, amino acids or minerals, without being limited thereto.

The film forming agent, the cosmetic composition or the cosmetic may include other solvents, thinners or additives depending on applications.

Here, the solvent or thinner component may be exemplified depending on applications of the composition, use forms, and the like, for example, by alcohols (e.g., polyethylene glycol, etc.), ethers (diethyl ether, etc.), glycol ethers (cellosolve species such as methyl cellosolve; dialkyleneglycol alkyl ethers such as diethylene glycol ethyl ether, etc.), nitriles (acetonitrile, etc.), ketones (acetone, etc.) or esters (carboxylic acid alkyl esters such as ethyl acetate, etc.).

In addition, the additive may be exemplified by not only plasticizer, wetting agents, antifoaming agents, coloring agents, preservatives, aromatics, flavors, pigments or thickeners but also common components used in quasi-drugs, pharmaceuticals or cosmetics, for example, powdery base materials or carriers (binders, disintegrants, excipients or lubricants and the like), oily base materials or carriers (animal and vegetable oils, waxes, vaseline, paraffin oils, silicone oils, higher fatty acid esters or higher fatty acids, etc.), aqueous base materials or carriers (gel base materials, such as xanthan gum, etc.), preservatives, chelating agents, antioxidants, refreshing agents, stabilizers, fluidizers, emulsifiers, thickeners, buffering agents, dispersing agent, absorbents, moisturizing agents, wetting agents, desiccants, antistatic agents or other resins (polyamide-based resins, olefin-based resins such as hydrogenated polybutene, etc.), without being limited thereto.

The method for preparing the film forming agent, the cosmetic composition or the cosmetic using the above components or other known additional components, if necessary is not particularly limited, and a known manner may be applied.

Advantageous Effects

The present application can provide a functional polymer showing a low solubility in polar and non-polar solvents. The polymer of the present application may be applied to various uses, and for example, when it is applied to cosmetics such as mascara, or other medicinal uses, it may represent a resistance to various solvents, such as sebum, sweat and tears, so that it may be used in a film forming agent, a cosmetic composition or a cosmetic capable of maintaining durability such as makeup.

MODE FOR INVENTION

Hereinafter, the polymers of the present application and the like will be specifically explained through Examples and Comparative Examples, but the scope of the polymer is not limited to the following examples. In Examples and Comparative Examples below, each physical property was evaluated by the following methods.

1. Solubility Measurement of Polymer

Polymer solutions prepared in Examples or Comparative Examples are kept at a temperature of about 150° C. for about 60 minutes to volatilize the solvent. 1 g of the polymer volatilizing the solvent is collected. 1 g of the above collected polymer is added to 5 g of a solvent (hexane, ethyl acetate, acetone or water) and stirred at room temperature for 30 minutes, and then the remaining polymer, which is un-dissolved, is removed. The transparent solution with removing the remaining polymer is sampled and dried at 150° C. for 30 minutes to remove the solvent. Through mass comparison of the remaining polymer in the solution removing the solvent the solid content is calculated. The concentration of the polymer dissolved in the solvent is measured through the solid content and the solubility is obtained by converting the measured amount to a value for 100 g of the solvent. If the solution is not transparent even after removing the remaining polymer, the solution is passed through a filter (0.45 μm NYLON) to obtain the transparent solution, and then the above process is carried out.

<Solubility Evaluation Criteria>

A: when the solubility is 15 or more
B: when the solubility is more than 10 and less than 15
C: when the solubility is more than 5 and up to 10
D: when the solubility is up to 5

2. Molecular Weight Measurement

The weight average molecular weight (Mw) and molecular weight distribution (PDI) were measured under the following conditions by using GPC, and the measurement results were converted by using the standard polystyrene of Agilent system in preparing a calibration curve.

<Measurement Conditions>

Measuring instrument: Agilent GPC (Agilent 1200 series, U.S.)
Column: PL Mixed B two connected
Column temperature: 40° C.
Eluant: THF (Tetrahydrofuran)
Flow rate: 1.0 mL/min
Concentration: ~1 mg/mL (100 μL injection)

3. Calculation of glass transition temperature

The glass transition temperature (Tg) was calculated depending on the monomer composition by the following Equation.

$$1/Tg = \Sigma Wn/Tn \qquad \text{<Equation>}$$

wherein Wn is a weight fraction of each monomer in the polymer, Tn is a glass transition temperature appearing when the monomer has formed a homopolymer, and the right-hand side of the equation is a result of summing all the calculated values after calculating the value (Wn/Tn) obtained by dividing the weight fraction of the used monomer by the glass transition temperature appearing when the monomer has formed a homopolymer for each monomer.

4. Sebum Blurring Test

Composition A is prepared by dissolving a polymer prepared in each preparation example in isododecane as a solvent in a concentration of about 10% by weight, and dissolving ceresine, a synthetic wax and a microcrystalline wax in concentrations of 7% by weight, 6% by weight and 8% by weight, respectively at a temperature of about 90° C. Subsequently, Composition B is prepared by adding propylene carbonate and disteardimonium hectorite to the Composition A in concentrations of 8% by weight and 2% by weight, respectively and dispersing them uniformly for 20 minutes. Subsequently, iron oxide (CI 77499) is added thereto in a concentration of 6% by weight and then an appropriate amount of preservatives is added, followed by being dispersed for 30 minutes and then slowly cooled to about 28° C., to prepare a mascara formulation.

Sebum blurring test using the prepared mascara formulation was divided into an in-vitro test and an in-vivo test and carried out, the details of which are as follows.

In-Vitro Test

The mascara formulation is applied on a slide glass (glass plate) to a thickness of 30 μm and then completely dried at room temperature. After drying, water and sebum are dropped on the mascara by 0.1 g, respectively, and after being left to stand for 20 minutes, a cotton pad is placed thereon and reciprocated 30 times with a force of 200 gf, and then the degrees of being smeared on the cotton pad are compared and evaluated in accordance with the following criteria.

<Evaluation Criteria>

When the degrees of being smeared on the cotton pad were compared on a scale within a range of 0 to 5, by setting the case of smearing no mascara at all on the cotton pad to 5 and setting the case of applying the polymer of the following comparative example 1 as a control group (reference) to 3, the superior level relative to the control group was quantified to one decimal place as a relative comparison between samples.

In-Vivo Test:

Images are taken 6 hours after applying the prepared mascara formulation on eyelashes of a test subject, compared and evaluated according to the following criteria.

<Evaluation Criteria>

After a lapse of 6 hours, images are taken and shown as values by image-analyzing blurring areas. On image-analyzing, the area of blurring was quantified as a pixel unit and shown.

5. Water Resistance Test

The above prepared mascara formulation is applied on a slide glass (glass plate) to a thickness of 30 μm and then completely dried at room temperature, and the dried sample is immersed in water at room temperature for about 30 minutes and then taken out to evaluate the water resistance depending on the following criteria according to mass decrease rates (=100×(1−B/A), unit:%, wherein A is the total mass of the slide glass applying the mascara formulation and B is the total mass of the slide glass measured after immersing it in water, then taking out and removing moisture).

<Evaluation Criteria>

A: when the mass decrease rate is at least 5%
B: when the mass decrease rate exceeds 5%

6. NMR Evaluation Method 0.1 g of the polymer solution prepared in Examples or Comparative Examples is collected and dissolved in 1 mL of the following solvent for NMR, and $^1$H-NMR is measured according to the manufacturer's manual by using the following analysis instrument, whereby the components and conversion rate of the polymer can be identified. For example, when the non-polymerized monomer is present, a —H peak derived from =CH2 of a double bond terminus in 1H-NMR spectrum is identified near at about 5.7 ppm to 6.4 ppm, and it is possible to identify the components of the prepared polymer through the area of —H peaks derived from each polymer structure.

<Measurement Conditions>
Analysis instrument: 500 MHz NMR (Varian Unity Inova 500), 1H-NMR
Concentration: 10~20 mg/mL, solvent: CDCl3-d3
Temperature: 25° C.

Example 1

As shown in Table 1 below, a monomer mixture in which EHMA (ethylhexyl methacrylate), IBOMA (isobornyl methacrylate) and EOEOEA (ethoxyethoxyethyl acrylate) were mixed in a weight ratio (EHMA:IBOMA:EOEOEA) of 25:60:15 was introduced into isododecane as a solvent to have the total monomer concentration of 35% by weight, and subsequently, the dissolved oxygen was removed by bubbling with nitrogen at room temperature for about 30 minutes together with stirring and the nitrogen bubbling was further carried out for about 40 minutes while elevating the reaction mixture removing oxygen to a temperature of about 70° C. If the temperature increased to 70° C. through the above process, the polymerization reaction proceeded while further introducing an appropriate amount of a thermal initiator (V-65) into isododecane as a solvent. After performing the reaction for about 24 hours, the reaction was completed by decreasing the temperature to room temperature to obtain a polymer solution.

Examples 2 to 4 and Comparative Examples 1 to 3

The polymer solutions were obtained in the same manner as Example 1 except that the monomer types and proportions of the monomer mixture were changed as Table 1 below.

TABLE 1

|  | Example | | | | Comparative Example | | |
| --- | --- | --- | --- | --- | --- | --- | --- |
|  | 1 | 2 | 3 | 4 | 1 | 2 | 3 |
| Polymer | A | B | C | D | E | F | G |
| EHA |  | 15 |  |  |  |  |  |
| LMA |  |  | 20 | 15 |  |  | 12 |
| EHMA | 30 |  |  |  |  |  |  |
| CHMA |  | 75 |  |  |  |  |  |
| IBOMA | 60 |  | 74 | 75 |  |  | 66 |
| EOEOEA | 10 | 10 |  | 10 |  |  | 10 |
| PEGMA |  |  | 6 |  |  |  | 12 |
| TMSS |  |  |  |  | 100 |  |  |
| PVP |  |  |  |  |  | 100 |  |
| Mw | 34 | 30 | 20 | 20 | — | — | — |
| Tg | 39 | 31 | 38 | 42 | 40 | 175 | — |

Content unit: g
EHA: ethyl hexyl acrylate (homopolymer solubility parameter: 8.4 $(cal/cm^3)^{1/2}$)
LMA: lauryl methacrylate (homopolymer solubility parameter: 8.2 $(cal/cm^3)^{1/2}$)
EHMA: ethylhexyl methacrylate (homopolymer solubility parameter: 8.3 $(cal/cm^3)^{1/2}$)
CHMA: cyclohexyl methacrylate (homopolymer solubility parameter: 7.9 $(cal/cm^3)^{1/2}$)
IBOMA: isobornyl methacrylate (homopolymer solubility parameter: 8.1 $(cal/cm^3)^{1/2}$)
EOEOEA: ethoxyethoxy ethylacrylate (homopolymer solubility parameter: 10.6 $(cal/cm^3)^{1/2}$)
PEGMA: polyethyleneglycol monoethyl ether methacrylate (ethylene oxide unit addition mole: 9 moles, homopolymer solubility parameter: 10.8 $(cal/cm^3)^{1/2}$)
TMSS: trimethylsiloxysilicate (homopolymer solubility parameter: 7.5 $(cal/cm^3)^{1/2}$) (Trimethyl siloxysilicate: Dow Corning MQ-1600 Resin)
PVP: polyvinyl pyrrolidone (homopolymer solubility parameter: 11 $(cal/cm^3)^{1/2}$, Aldrich K30)
Mw: weight average molecular weight (×10000)
Tg: glass transition temperature (unit: ° C.)

1. Evaluation of NMR

As a result of evaluating NMR for the polymer of Example 1 1H peaks derived from =CH2 of the double bond terminus were little identified, whereby it can be confirmed that the polymerization has been carried out effectively. In addition, —CH— peaks adjacent to —COO— of EHMA and IBOMA forming the polymer and peaks derived from —OCH2CH2O— of EOEOEA were observed in the region of 5.0 μm to 3.5 ppm, where an area value of peaks is 9. Furthermore, peaks derived from —CH2- of the side chain and —CH3 derived from the meta-position were identified in the region of 2.5 ppm to 1.3 ppm as peaks having an area value of 36, and 1H peaks identified from —CH2CH— and —CH2CH2- derived from the polymer backbone, were identified in the region of 1.3 ppm to 0.5 ppm as an area of 55.

For the polymer of Example 2, NMR was also equally evaluated. As a result of evaluation, 1H peaks derived from =CH2 of the double bond terminus were little identified, whereby it could be confirmed that the polymerization has been carried out efficiently. In addition, —CH— peaks adjacent to —COO— of EHA and CHMA forming the polymer and peaks derived from —OCH2CH2O— of EOEOEA were identified in the region of 4.8 ppm to 3.4 ppm as an area value of 10. Furthermore, from —CH2- adjacent to —COO— of EHA forming the polymer, peaks having an area value of about 3 were identified in the region o 2.5 ppm to 2.0 ppm, and from —CH2- of the side chain and —CH3 derived from the meta-position, peaks having an area value of 57 were identified in the region of 2.0 ppm to 1.5 ppm. Furthermore, 1H area value identified from —CH2CH— and —CH2CH2- derived from the polymer backbone was about 29 in 1.5 ppm to 0.5 ppm.

In the case of the polymer of Example 3, 1H peaks derived from =CH2 of the double bond terminus were little identified. In addition, —CH2- and —CH— peaks adjacent to —COO— of LMA and IBOMA forming the polymer and peaks derived from —OCH2CH2-O and —OCH3 of PEGMA appeared in the region of 4.7 ppm to 3.3 ppm, and the area value of the peaks was 17. Furthermore, peaks from —CH2- of the side chain and —CH3 derived from the meta-position were identified in the region of 2.0 ppm to 1.5 ppm as an area value of 72, and the area value of 1H peaks identified from —CH2CH— derived from the polymer backbone was 11 in the region of 1.5 ppm to 0.5 ppm.

In results of measuring NMR for the polymer of Example 4, 1H peaks derived from =CH2 of the double bond terminus were also little observed. In addition, —CH2- and —CH— peaks adjacent to —COO— of LMA and IBOMA forming the polymer and peaks derived from —OCH2CH2O— of EOEOEA appeared in the region of 4.7 ppm to 3.3 ppm, and the area value of the peaks was 9. Furthermore, from —CH2- of the side chain and —CH3 derived from the meta-position, peaks having an area value of 36 were identified in the region of 2.0 ppm to 1.5 ppm, and 1H area value identified from —CH2CH— and —CH2CH2- derived from the polymer backbone was 55 in 1.5 ppm to 0.5 ppm.

Meanwhile, in the case of Comparative Example 3, the polymerization between monomers was not appropriately achieved, and monomers and the like were precipitated in the polymerization process, and thus the synthesis of the polymer was impossible.

2. Physical Property Evaluation Results

The results of measuring physical properties for each polymer of Examples and Comparative Examples were summarized and described in Table 2 below.

TABLE 2

| | | Example | | | | Comparative Example | |
|---|---|---|---|---|---|---|---|
| | | 1 | 2 | 3 | 4 | 1 | 2 |
| Polymer | | A | B | C | D | E | F |
| Solubility | Hexane | D | C | D | D | A | D |
| | Ethyl acetate | A | A | A | A | A | D |
| | Acetone | C | D | D | D | A | D |
| | Water | D | D | D | D | D | A |
| Sebum blurring | In-vitro | 3.9 | 4.0 | 3.8 | 4.0 | 3.0 | 3.3 |
| | In-vivo | 3200 | 3100 | 3200 | 3000 | 4500 | 3800 |
| Water resistance test | | A | A | A | A | A | B |

It can be confirmed from the above results that in the case of the polymer satisfying the requirements of the present application, it exhibits a low solubility in polar solvents (water, acetone) and non-polar solvents (hexane) and exhibits an excellent solubility in solvents (ethyl acetate) having middle characteristics. Also, if such a polymer was applied, it was confirmed to have an excellent sebum resistance even in the sebum blurring test while securing water resistance.

The invention claimed is:

1. A polymer comprising polymerized units of a first monomer having a homopolymer solubility parameter of in a range of 5 $(cal/cm^3)^{1/2}$ to 9.5 $(cal/cm^3)^{1/2}$ and polymerized units of a second monomer having a homopolymer solubility parameter of 10.0 $(cal/cm^3)^{1/2}$ or more, wherein the second monomer is a compound represented by Formula 2 or 3 below:

[Formula 2]

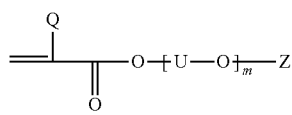

wherein Q is hydrogen or an alkyl group, U is an alkylene group, Z is hydrogen or an alkyl group, and m is a number in a range of 1 to 100,

[Formula 3]

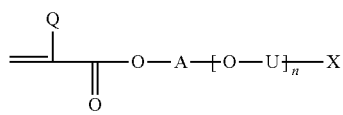

wherein Q is hydrogen or an alkyl group, A and U are each independently an alkylene group, X is a hydroxy group or a cyano group, and n is a number in a range of 1 to 100, wherein the polymer comprises at least 75 parts by weight of the polymerized units of the first monomer, and wherein the solubility of the polymer at room temperature is 10 or less in a solvent having a dielectric constant (25° C.) in a range of 1 to 3, and the solubility of the polymer at room temperature is 10 or less in a solvent having a dielectric constant (25° C.) in a range of 75 to 85.

2. The polymer according to claim 1, wherein the solubility at room temperature is 5 or less in a solvent having a dielectric constant (25° C.) in a range of 1 to 3.

3. The polymer according to claim 1, wherein the solubility at room temperature is 5 or less in a solvent having a dielectric constant (25° C.) in a range of 75 to 85.

4. The polymer according to claim 1, wherein the solubility at room temperature is 15 or more in a solvent having a dielectric constant (25° C.) in a range of 4 to 15.

5. The polymer according to claim 1, wherein the first monomer has a homopolymer solubility parameter in a range of 7 $(cal/cm^3)^{1/2}$ to 9 $(cal/cm^3)^{1/2}$.

6. The polymer according to claim 1, wherein the first monomer is alkyl (meth)acrylate or aromatic (meth)acrylate.

7. The polymer according to claim 1, wherein the first monomer is a compound represented by Formula 1 below:

[Formula 1]

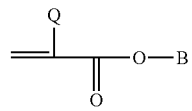

wherein, Q is hydrogen or an alkyl group, B is a straight or branched alkyl group having 4 or more carbon atoms, an alicyclic hydrocarbon group, or an aromatic substituent.

8. The polymer according to claim 7, wherein the aromatic substituent is an aryl group or an arylalkyl group.

9. The polymer according to claim 7, wherein in Formula 1 Q is hydrogen or a methyl group and B is an alkyl group having 7 or more carbon atoms or an alicyclic hydrocarbon group having 6 to 18 carbon atoms.

10. The polymer according to claim 1, wherein the second monomer has a homopolymer solubility parameter in a range of 10.0 $(cal/cm^3)^{1/2}$ to 15.0 $(cal/cm^3)^{1/2}$.

11. The polymer according to claim 1, wherein the second monomer has a homopolymer solubility parameter in a range of 10.0 $(cal/cm^3)^{1/2}$ to 13.0 $(cal/cm^3)^{1/2}$.

12. The polymer according to claim 1, wherein in Formula 2 Q is hydrogen or an alkyl group having 1 to 4 carbon atoms, U is an alkylene group having 1 to 4 carbon atoms, Z is hydrogen or an alkyl group having 1 to 4 carbon atoms and m is a number in a range of 1 to 30.

13. The polymer according to claim 1, wherein the polymer comprises 0.1 to 20 parts by weight of the polymerized units of the second monomer.

14. The polymer according to claim 1, wherein the polymer comprises 75 to 99.9 parts by weight of the polymerized units of the first monomer and 5 to 20 parts by weight of the polymerized units of the second monomer.

15. A film forming agent comprising the polymer of claim 1.

* * * * *